United States Patent [19]

Pitt et al.

[11] 4,072,745
[45] * Feb. 7, 1978

[54] SUBSTITUTED VINYL THIOPHOSPHATE ACTIVATORS

[75] Inventors: Leland S. Pitt, Greenville, Miss.; George B. Large, Orinda, Calif.

[73] Assignee: Stauffer Chemical Company, Westport, Conn.

[*] Notice: The portion of the term of this patent subsequent to May 27, 1992, has been disclaimed.

[21] Appl. No.: 665,987

[22] Filed: Mar. 11, 1976

[51] Int. Cl.$^2$ .............................................. A01N 9/36
[52] U.S. Cl. ............................ 424/200; 260/340.5 R; 260/951; 260/955; 260/957
[58] Field of Search ..................... 260/951, 955, 340.5, 260/957; 424/200

[56] References Cited

U.S. PATENT DOCUMENTS

| | | | |
|---|---|---|---|
| 3,021,352 | 2/1962 | Miller | 424/219 |
| 3,116,201 | 12/1963 | Whetstone et al. | 424/219 |
| 3,557,258 | 1/1971 | Beriger et al. | 260/951 |
| 3,821,246 | 6/1974 | Kishino et al. | 424/200 X |
| 3,886,273 | 5/1975 | Large et al. | 424/200 |
| 3,898,306 | 8/1975 | Böger et al. | 260/951 |
| 3,969,442 | 7/1976 | Böger et al. | 260/951 |

FOREIGN PATENT DOCUMENTS 4,627,280   7/1971   Japan ................................. 424/200

*Primary Examiner*—Ethel G. Love
*Attorney, Agent, or Firm*—M. Henry Heines; Daniel C. Block

[57] ABSTRACT

Compounds which are useful as insecticide activators are described herein. The compounds are defined by the following formula:

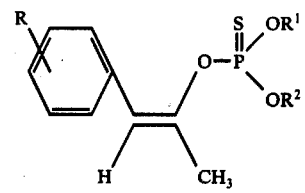

wherein R is selected from the group consisting of chlorine, trifluoromethyl, methoxy, and methylenedioxy; and R$^1$ and R$^2$ can be the same or different and are selected from the group consisting of lower alkyl having from 1 to 4 carbon atoms, inclusive.

32 Claims, No Drawings

SUBSTITUTED VINYL THIOPHOSPHATE ACTIVATORS

BACKGROUND OF THE INVENTION

Among the many insecticidal compounds, the phthalimidothiophosphates have reached a relatively high degree of commercial success. These compounds are toxic to a large number of insect pests at different concentrations varying with the resistance of the insects. Some of these compounds are described in U.S. Pat. No. 2,767,194, specifically ·N-(mercaptomethyl) phthalimide S-(O,O-dimethylphosphorodithioate).

The endeavor to extend the usefulness of the thiophosphates by increasing their effectiveness and lowering their cost has led to extensive studies on another class of biologically active chemicals, customarily referred to as activators. Among the many activators employed, the alkyl oxides, specifically piperonyl butoxide, have been widely used. These compounds are described in U.S. Pat. Nos. 2,485,681 and 2,550,737. In addition, vinyl thionophosphates containing an unsubstituted phenyl group have been found to be effective activators. These compounds are described in U.S. Pat. Nos. 3,380,887 and 3,886,273.

BRIEF DESCRIPTION OF THE INVENTION

It has been discovered that the activity of insecticidally active thiophosphate compounds can be enhanced by using an activator having the formula

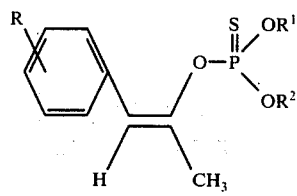

wherein R is selected from the group consisting of chlorine, trifluoromethyl, methoxy, and methylenedioxy; and $R^1$ and $R^2$ can be the same or different and are selected from the group consisting of lower alkyl having from 1 to 4 carbon atoms, inclusive.

DETAILED DESCRIPTION OF THE INVENTION

The compounds of the present invention are manufactured by reacting an appropriate substituted phenyl acetone with an appropriate haloalkyl phosphoro derivative. These raw materials are commercially available compounds. When the end products are achieved, they are isolated, purified, and admixed with the insecticidal thiophosphate compound. The amount of activator admixed therewith can range from about 1:0.1 to about 1:10 parts insecticidal compound to activator compound. The insecticide-activator mixture is applied to the habitat of the insect in a conventional manner.

In order to illustrate the merits of the present invention, the following examples are provided:

EXAMPLE 1

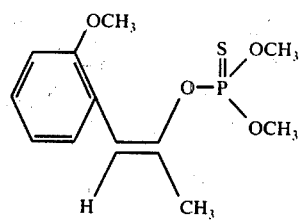

To a stirring mixture of 1.2 g (0.05 mole) sodium hydride in 50 ml anhydrous tetrahydrofuran was added 8.2 g (0.05 mole) o-methoxyphenyl acetone, in a dropwise manner. When the addition was complete, the temperature of the mixture was increased to 40° C for 1 hour. To the resulting clear solution was added 8.0 g (0.05 mole), O,O-dimethylchloridophosphorothioate. The mixture was refluxed for 1 hour, then cooled and diluted with an equal volume of benzene. The solution was then washed three times with water and dried over anhydrous magnesium sulfate. The solvent was stripped in vacuo to yield 13.5 g (83% yield) of product with refractive index $n_D^{30} = 1.5448$.

EXAMPLE 2

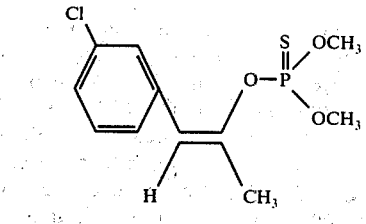

The procedure described in Example 1 was repeated in its entirety except that m-chlorophenyl acetone was used instead of o-methoxyphenyl acetone to yield 8.2 g (93% yield) of product, with refractive index $n_D^{30} = 1.5573$.

Additional compounds were synthesized in a similar manner using appropriate starting materials. These compounds are listed in the following table.

TABLE I

| | | $n_D^{30}$ |
|---|---|---|
| Example 3 | ![Cl-substituted structure] | 1.5496 |
| Example 4 | ![Cl-substituted structure] | 1.5474 |

TABLE I-continued

| | | $n_D^{30}$ |
|---|---|---|
| Example 5 | (CF₃-phenyl-CH(CH₃)-O-P(=S)(OCH₃)(OCH₃), with H on vinyl carbon) | 1.4906 |
| Example 6 | (methylenedioxyphenyl-CH(CH₃)-O-P(=S)(OCH₃)(OCH₃), with H on vinyl carbon) | 1.5468 |
| Example 7 | (CH₃O-phenyl-CH(CH₃)-O-P(=S)(OCH₃)(OCH₃), with H on vinyl carbon) | 1.5266 |

INSECTICIDE EVALUATION

A. Housefly [*Musca domestica* (L.)]

Test compounds either alone or in combination with the toxicant are diluted in acetone and aliquots are pipetted onto the bottom of 55 × 15 mm aluminum dishes. To insure even spreading of the chemicals on the bottom of the dishes, 1 ml of acetone containing 0.02% peanut oil is also added to each dish. After all solvents have evaporated the dishes are placed in circular cardboard cages containing 25 3-day old female houseflies. The cages are covered on the bottom with cellophane and the top with tulle netting, and each contains a sugar-water saturated cotton plug for maintenance of the flies. Mortality is recorded after 48 hours. Test levels range from 100 μg/25 female houseflies down to that at which approximately 50% mortality occurs.

B. Tobacco Budworm [*Heliothis virescens* (F.)]

Test compounds either alone or in combination with the toxicant are diluted in a 50-50 acetone-water solution. Sections of Romaine lettuce (*Latuca sativa*) leaves, approximately 1×1.5 inches, are immersed in the test solutions for 2-3 seconds and placed on a wire screen to dry. The dried leaves are placed in petri dishes containing a moistened piece of filter paper and infested with five second-instar tobacco budworm larvae. Mortality of the larvae is recorded 48 hours later, and a piece of synthetic media is added to dishes containing survivors. These are then held for 5 additional days to observe for any delayed effects of the test chemicals. Test concentrations range from 0.1% to that at which approximately 50% mortality occurs.

C. Cabbage Looper [*Trichoplusia ni*]

The procedure is the same as that used for the Tobacco Budworm, except that cotyledons of squash [*Curcurbita pepo*] are utilized as the host plant rather than Romaine lettuce leaves.

D. Green Peach Aphid [*Myzus persicae* (Sulzer)]

Radish plants (*Rhaphanus sativus*), approximately 2 cm tall, are transplanted into sandy loam soil in 3 inch clay pots and infested with 25-50 green peach aphids of mixed ages. Twenty-four hours later they are sprayed, to the point of runoff, with 50-50 acetone-water solutions of the test chemicals. Treated plants are held in the greenhouse and mortality is recorded after 48 hours. Test concentrations range from 0.05% down to that at which 50% mortality occurs.

E. German Cockroach [*Blatella germanica* (Linné)]

Test compounds either alone or in combination with the toxicant are diluted in a 50-50 acetone-water solution. Two cc of the solution are sprayed through a DeVilbiss type EGA hand spray gun into circular cardboard cages containing 10 1-month old German cockroach nymphs. The test cages are covered on the bottom with cellophane and the top with tulle netting. Per cent mortality is recorded 2 days later. Test concentrations range from 0.1% down to that at which 50% mortality occurs. All $LD_{50}$ values are expressed as per cent toxicant.

Activating Factor

The activating factor (A.F.) is computed by the following formula:

$$A.F. = \frac{LD_{50} \text{ of Toxicant} \left(\frac{1}{XY+1}\right)}{\text{Experimental } LD_{50} \text{ of Combination.}}$$

where

X = the weight ratio of activator to toxicant, and
Y = the ratio of the $LD_{50}$ of the toxicant to the $LD_{50}$ of the activator.

The experimental $LD_{50}$ of the combination is in terms of the toxicant only.

The activating factor is therefore the expected $LD_{50}$ of the combination divided by the experimental $LD_{50}$. It is noted that when the observed response is greater than the expected, the activating factor is greater than one. When this result is observed, the toxicant has been activated.

The results of the evaluation tests described above are set forth in the following table.

TABLE II

CONTACT ACTIVITY: APPROXIMATE $LD_{50}$ VALUES

HF: Housefly
TB: Tobacco Budworm
CL: Cabbage Looper
GPA: Green Peach Aphid
GC: German Cockroach Toxicant: N-(Mercaptomethyl)phthalimide S-(O,O-dimethyl phosphorodithioate)

| | HF ug/25 ♀ | TB % | CL % | GPA % | GC % |
|---|---|---|---|---|---|
| Activator:Toxicant | | | | | |

TABLE II-continued
CONTACT ACTIVITY: APPROXIMATE LD$_{50}$ VALUES

| | | |
|---|---|---|
| HF: | Housefly | |
| TB: | Tobacco Budworm | |
| CL: | Cabbage Looper | |
| GPA: | Green Peach Aphid | |
| GC: | German Cockroach | |

Toxicant: N-(Mercaptomethyl)phthalimide S-(O,O-dimethyl phosphorodithioate)

| | HF ug/25 ♀ | TB % | CL % | GPA % | GC % |
|---|---|---|---|---|---|
| weight ratio | 1:5 | 1:1 | 1:1 | 1:1 | 1:1 |
| Toxicant Alone | 3.5 | .5 | .07 | .03 | .04 |
| Toxicant + Example 1 | 3.5 | .003 | .07 | .007 | .02 |
| Example 1 Alone | >100 | .1 | >.1 | >.1 | >.1 |
| Activating Factor | >1.0 | 27.8 | >1.0 | >3.3 | >1.4 |
| Toxicant + Example 2 | 3.0 | .007 | .07 | .02 | .02 |
| Example 2 Alone | >100 | .05 | >.1 | >.1 | >.1 |
| Activating Factor | >1.2 | 6.5 | >1.0 | >1.2 | >1.4 |
| Toxicant + Example 3 | 2.0 | .007 | .007 | .01 | .02 |
| Example 3 Alone | >100 | >.1 | >.1 | >.1 | >.1 |
| Activating Factor | >1.7 | >11.9 | >5.9 | >2.3 | >1.4 |
| Toxicant + Example 4 | 3.0 | .008 | .07 | .007 | .01 |
| Example 4 Alone | >100 | >.1 | >.1 | >.1 | >.1 |
| Activating Factor | >1.2 | >10.4 | >1.0 | >3.3 | >2.9 |
| Toxicant + Example 5 | 2.5 | | .07 | .02 | .03 |
| Example 5 Alone | >100 | | >.1 | >.1 | >.1 |
| Activating Factor | >1.4 | | >1.0 | >1.2 | >1.0 |
| Toxicant Alone | | .1 | .03 | .003 | .03 |
| Toxicant + Example 6 | | .05 | .008 | .0008 | .02 |
| Example 6 Alone | | >.1 | >.1 | .1 | >.1 |
| Activating Factor | | >1.0 | >29 | 3.6 | >1.2 |
| Toxicant + Example 7 | | >.1 | .005 | .003 | .02 |
| Example 7 Alone | | >.1 | .1 | >.1 | >.1 |
| Activating Factor | | 0.55 | 4.6 | >1.0 | >1.2 |

The compositions of this invention are generally embodied, in formulations suitable for convenient application. In general, such formulations will contain inert or occasionally active ingredients or diluent carriers in addition to the active compound. Examples of such ingredients or carriers are organic solvents, such as sesame oil, xylene range solvents, and heavy petroleum; water; emulsifying agents; surface active agents; talc; pyrophyllite; diatomite; gypsum; clays; and propellants, such as dichlorodifluoromethane.

The active compositions can be combined with dust carriers for application as dusts, with granular carriers for application by fertilizer spreaders or ground or airplane seeders, with wettable powders or flowable carriers for application as water suspensions, and with solvents and surface active materials for application as sprays, aerosols, or emulsions. The compositions can be applied to any habitat of the pests, for example, dwellings, clothing, plant and insect surfaces; soil, etc. If desired, however, the active compositions can be applied directly to feedstuffs, seeds, etc., upon which the pests feed. When applied in such a manner, it will be advantageous to use a composition which is not volatile.

The amount of active composition or formulation which is considered to be insecticidally effective is that amount which, when applied to the pest habitat, will kill or substantially injure a significant portion residing thereon. The amount of activator which is considered to be effective is that amount which, when in combination with the insecticidally active thiophosphate compound, results in a composition of matter whose insecticidal activity is greater that than of either of its components when the latter are applied individually.

In connection with the activity of the presently disclosed pesticidal compositions, it should be fully understood that it is not necessary that they be active as such. The purposes of this invention will be fully served if the composition is rendered active by external influences, such as light, or by some physiological action which occurs when the preparation is ingested or penetrates into the body of the pest.

The presice manner in which the pesticidal compositions of this invvention are used in any particular instance will be readily apparent to a person skilled in the art. Generally, the active pesticidal composition will be embodied in the form of a liquid composition; for example, an emulsion, suspension, or aerosol spray. While the concentration of the active pesticide composition in the present formulation can vary within rather wide limits, ordinarily, the pesticide composition will comprise not more than about 50.0% by weight of the formulation.

What is claimed is:

1. A compound having the formula

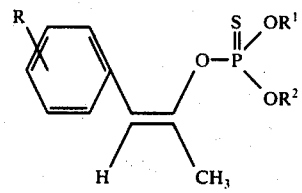

wherein R is selected from the group consisting of chlorine, trifluoromethyl, methoxy, and methylenedioxy; and $R^1$ and $R^2$ can be the same or different and are selected from the group consisting of lower alkyl having from 1 to 4 carbon atoms, inclusive.

2. A compound according to claim 1 in which R is 2-methoxy, $R^1$ is methyl, and $R^2$ is methyl.

3. A compound according to claim 1 in which R is 3-chloro, $R^1$ is methyl, and $R^2$ is methyl.

4. A compound according to claim 1 in which R is 2-chloro, $R^1$ is methyl, and $R^2$ is methyl.

5. A compound according to claim 1 in which R is 4-chloro, $R^1$ is methyl, and $R^2$ is methyl.

6. A compound according to claim 1 in which R is 3-trifluoromethyl, $R^1$ is methyl, and $R^2$ is methyl.

7. A compound according to claim 1 in which R is 3,4-methylenedioxy, $R^1$ is methyl, and $R^2$ is methyl.

8. A compound according to claim 1 in which R is 4-methoxy, $R^1$ is methyl, and $R^2$ is methyl.

9. An insecticidally active composition comprising an insecticidally effective amount of an insecticide defined as N-(mercaptomethyl) phthalimide S-(O,O-dimethylphosphorodithioate) and an effective amount of an activator having the formula

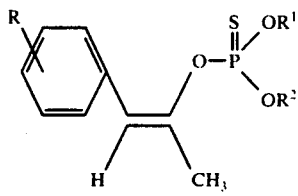

wherein R is selected from the group consisting of chlorine, trifluoromethyl, methoxy, and methylenedioxy, and $R^1$ and $R^2$ can be the same or different and are selected from the group consisting of lower alkyl having from 1 to 4 carbon atoms, inclusive; said activator being present in an amount ranging between 0.1 and 10 parts by weight per each part by weight insecticide.

10. The composition of claim 9 in which R is 2-methoxy, $R^1$ is methyl, and $R^2$ is methyl.

11. The composition of claim 9 in which R is 3-chloro, $R^1$ is methyl, and $R^2$ is methyl.

12. The composition of claim 9 in which R is 2-chloro, $R^1$ is methyl, and $R^2$ is methyl.

13. The composition of claim 9 in which R is 4-chloro, $R^1$ is methyl, and $R^2$ is methyl.

14. The composition of claim 9 in which R is 3-trifluoromethyl, $R^1$ is methyl, and $R^2$ is methyl.

15. The composition of claim 9 in which R is 3,4-methylenedioxy, $R^1$ is methyl, and $R^2$ is methyl.

16. The composition of claim 9 in which R is 4-methoxy, $R^1$ is methyl, and $R^2$ is methyl.

17. A method of controlling insects comprising applying to the habitat thereof an insecticidally effective amount of an insecticidally active composition comprisng an insecticide defined as N-(mercaptomethyl) phthalimide S-(O,O-dimethyl phosphorodithioate) and an effective amount of an activator having the formula

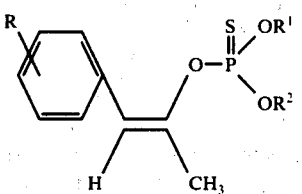

wherein R is selected from the group consisting of chlorine, trifluoromethyl, methoxy, and methylenedioxy; and $R^1$ and $R^2$ can be the same or different and are selected from the group consisting of lower alkyl having from 1 to 4 carbon atoms, inclusive; said activator being present in an amount ranging between 0.1 and 10 parts by weight per each part by weight insecticide.

18. The method of claim 17 in which R is 2-methoxy, $R^1$ is methyl, and $R^2$ is methyl.

19. The method of claim 17 in which R is 3-chloro, $R^1$ is methyl, and $R^2$ is methyl.

20. The method of claim 17 in which R is 2-chloro, $R^1$ is methyl, and $R^2$ is methyl.

21. The method of claim 17 in which R is 4-chloro, $R^1$ is methyl, and $R^2$ is methyl.

22. The method of claim 17 in which R is 3-trifluoromethyl, $R^1$ is methyl and $R^2$ is methyl.

23. The method of claim 17 in which R is 3,4-methylenedioxy, $R^1$ is methyl and $R^2$ is methyl.

24. The method of claim 17 in which R is 4-methoxy, $R^1$ is methyl and $R^2$ is methyl.

25. An insecticidally active composition comprising an inert diluent carrier, an insecticidally effective amount of an insecticide defined as N-(mercaptomethyl) phthalimide S-(O,O-dimethylphosphorodithioate) and an effective amount of an activator having the formula

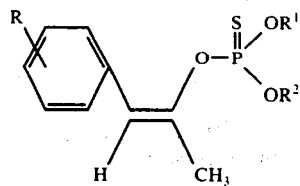

wherein R is selected from the group consisting of chlorine, trifluoromethyl, methoxy, and methylenedioxy; and $R^1$ and $R^2$ can be the same or different and are selected from the group consisting of lower alkyl having from 1 to 4 carbon atoms, inclusive; said activator being present in an amount ranging from between 0.1 and 10 parts by weight per each part by weight insecticide.

26. The composition of claim 25 in which R is 2-methoxy, $R^1$ is methyl, and $R^2$ is methyl.

27. The composition of claim 25 in which R is 3-chloro, $R^1$ is methyl, and $R^2$ is methyl.

28. The composition of claim 25 in which R is 2-chloro, $R^1$ is methyl, and $R^2$ is methyl.

29. The composition of claim 25 in which R is 4-chloro, $R^1$ is methyl, and $R^2$ is methyl.

30. The composition of claim 25 in which R is 3-trifluoromethyl, $R^1$ is methyl, and $R^2$ is methyl.

31. The composition of claim 25 in which R is 3,4-methylenedioxy, $R^1$ is methyl, and $R^2$ is methyl.

32. The composition of claim 25 in which R is 4-methoxy, $R^1$ is methyl, and $R^2$ is methyl.

* * * * *